US007909764B1

(12) United States Patent
Wenzel et al.

(10) Patent No.: US 7,909,764 B1
(45) Date of Patent: Mar. 22, 2011

(54) METHODS AND SYSTEMS TO MONITOR VENOUS BLOOD OXYGEN SATURATION

(75) Inventors: Brian Jeffrey Wenzel, San Jose, CA (US); Fujian Qu, Sunnyvale, CA (US); Taraneh Ghaffari Farazi, San Jose, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 780 days.

(21) Appl. No.: 11/948,381

(22) Filed: Nov. 30, 2007

(51) Int. Cl.
*A61B 5/00* (2006.01)
*A61B 5/04* (2006.01)

(52) U.S. Cl. ......... 600/309; 600/509; 600/513; 600/515

(58) Field of Classification Search .................. 600/309, 600/509, 510, 515, 607
See application file for complete search history.

(56) References Cited

U.S. PATENT DOCUMENTS

| 5,119,813 | A | 6/1992 | Cohen |
| 5,634,461 | A | 6/1997 | Faithfull et al. |
| 5,891,176 | A | 4/1999 | Bornzin |
| 6,188,927 | B1 | 2/2001 | Lu et al. |
| 6,321,101 | B1 | 11/2001 | Holmstrom |
| 7,164,948 | B2 | 1/2007 | Struble et al. |
| 2006/0009688 | A1 | 1/2006 | Lamego et al. |

OTHER PUBLICATIONS

Penneys and Thomas, "The Relationship between the Arterial Oxygen Saturation and the Cardiovascular Response to Induced Anoxemia in Normal Young Adults," Circulation, vol. 1, No. 3 (Mar. 1950).
Lau, et al., "Utility of an implantable right ventricular oxygen saturation-sensing pacemaker for ambulatory cardiopulmonary monitoring," Chest, vol. 107, 1089-1094 (1995).
Kayar et al., "Relationship between T-wave amplitude and oxygen pulse in guinea pigs in hyperbaric helium and hydrogen," Journal of Applied Physiology, vol. 85 , No. 3, pp. 798-806 (1998.
"Understanding Continuous Mixed Venous Oxygen Saturation (SvO2) Monitoring with The Edwards Swan-ganz Oximetry TD System, 2nd Edition," Edwards Lifesciences, pp. 1-20 (2002).

*Primary Examiner* — Long V Le
*Assistant Examiner* — Michael T Rozanski
(74) *Attorney, Agent, or Firm* — Steven M. Mitchell

(57) ABSTRACT

Methods and system are provided for monitoring a patients venous blood oxygen saturation (SvO2). At least one signal indicative of electrical activity of a patient's heart is obtained. Such a signal can be, e.g., an IEGM or ECG signal. In specific embodiments, such a signal(s) can be obtained from implanted electrodes, and thus, embodiments of the present invention can be implemented by an implantable system. Additionally, there are measurements of at least one metric of cardiac cycles represented in the at least one signal indicative of electrical activity of the patient's heart, where the metric changes with changes in SvO2. Examples of such metric include T-wave metrics and PR intervals. SvO2, and changes therein, are monitored based on the measured metric(s).

24 Claims, 12 Drawing Sheets

METHODS AND SYSTEMS TO MONITOR VENOUS BLOOD OXYGEN SATURATION

FIELD OF THE INVENTION

The present invention relates generally to implantable cardiac stimulation devices capable of monitoring venous oxygen saturation (SvO2) using an intracardiac electrogram (IEGM) or electrocardiogram (ECG).

BACKGROUND OF THE INVENTION

Implantable cardiac stimulation devices are currently being used to treat various types of arrhythmias, such as ventricular tachycardia (VT) and ventricular fibrillation (VF). Such devices are capable of detecting the occurrence of an arrhythmia, and automatically applying an appropriate electrical stimulation or shock therapy to the heart aimed at terminating the detected arrhythmia. In addition to providing automatic stimulation, such devices often include circuitry that is configured to acquire intracardiac electrogram (IEGM) signals, convert the raw analog data into digital signals, and store the digital signals for later processing and/or telemetric transmission to an external device.

Recently there has been increased interest in adding monitoring capabilities to implantable cardiac devices. For example, many publications have suggested attaching various types of implantable sensors to the housings of pacemakers and/or implantable cardioverter-defibrillators (ICDs), or adding such sensors to leads that attach to pacemakers and/or ICDs. Examples of such sensors include implantable venous oxygen saturation sensors, including implantable pulse oximetry sensors, which include implantable light sources and light detectors that can be used to monitor blood oxygen concentration levels. While such optical sensors are useful, they may add to the cost and complexity of implantable cardiac systems. Additionally, such optical sensors may cause an increased drain on device batteries, potentially reducing the longevity of such devices. Accordingly, it would be useful if alternative and potentially more efficient techniques for monitoring venous oxygen saturation were available. Preferably such techniques would require minimum changes to existing pacemakers and ICDs.

SUMMARY OF THE INVENTION

Embodiments of the present invention relate methods and system for monitoring a patient's venous blood oxygen saturation (SvO2). In accordance with specific embodiments, at least one signal indicative of electrical activity of a patient's heart is obtained. Such a signal can be, e.g., an IEGM or ECG signal. In specific embodiments, such a signal(s) can be obtained from implanted electrodes, and thus, embodiments of the present invention can be implemented by an implantable system. Additionally, there are measurements of at least one metric of cardiac cycles represented in the at least one signal indicative of electrical activity of the patient's heart, where the metric changes with changes in SvO2. Examples of such metric include T-wave metrics and PR intervals.

In accordance with specific embodiments, the above steps are repeated over time to thereby monitor changes in the patient's SvO2 over time. This can include interpreting increases in T-wave metrics and/or PR intervals as increases in the patient's SvO2, and interpreting decreases in such metrics as decreases in the patient's SvO2. Based on such monitored changes in SvO2, pacing rate and pacing interval optimization, or more generally pacing rate and pacing interval adjustments, can be performed. In other words, measures of SvO2, as determined from an IEGM and/or ECG, can be used as a measure of hemodynamic response in a pacing adjustment or optimization algorithm.

In accordance with further embodiments, changes in a patient's SvO2, as measured based on changes in metric(s) of a signal indicative of electrical activity of the patient's heart, can be used to monitor changes in a patient's heart failure (HF) condition. This can include interpreting decreases in the patient's SvO2 over time as being indicative of worsening of the patient's heart failure, and interpreting increases in the patient's SvO2 over time as being indicative of improvement of the patient's heart failure.

In accordance with specific embodiments of the present invention, anemic episodes are monitored for based on changes in the patient's SvO2, as monitored based on changes in at least one metric of a signal indicative of electrical activity of the patient's heart. This can include interpreting transient decreases in the patient's SvO2 as being indicative of anemic episodes.

In accordance with specific embodiments of the present invention, internal hemorrhaging is monitored for based on changes in the patient's SvO2, as monitored based on changes in at least one metric of a signal indicative of electrical activity of the patient's heart. This can include interpreting transient decreases in the patient's SvO2 as being indicative of internal hemorrhaging.

In accordance with specific embodiments of the present invention, episodes of sleep apnea are monitored for based on changes in the patient's SvO2, as monitored based on changes in at least one metric of a signal indicative of electrical activity of the patient's heart. This can include interpreting transient decreases in the patient's SvO2, while the patient is likely sleeping, as being indicative of episodes of sleep apnea.

This summary is not intended to be a complete description of the invention. Other features and advantages of the invention will appear from the following description in which the preferred embodiments have been set forth in detail, in conjunction with the accompanying drawings and claims.

DETAILED DESCRIPTION OF PREFERRED EMBODIMENTS

Figure 1:
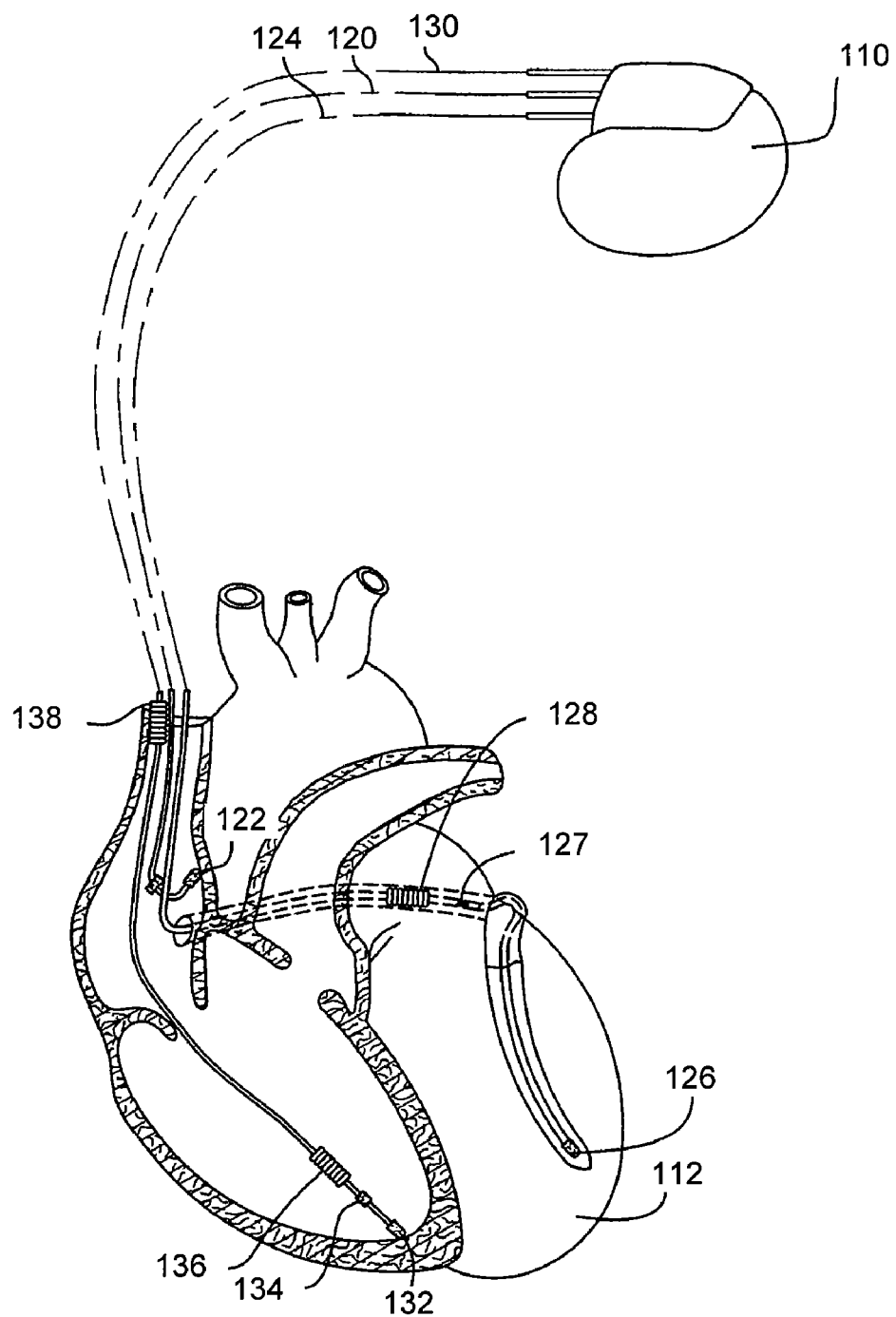
FIG. 1 is a simplified, partly cutaway view illustrating an implantable stimulation device in electrical communication with at least three leads implanted into a patient's heart for delivering multi-chamber stimulation and shock therapy.

The following description is of the best modes presently contemplated for practicing various embodiments of the present invention. The description is not to be taken in a limiting sense but is made merely for the purpose of describing the general principles of the invention. The scope of the invention should be ascertained with reference to the claims. In the description of the invention that follows, like numerals or reference designators will be used to refer to like parts or elements throughout. In addition, the first digit of a reference number identifies the drawing in which the reference number first appears.

The disclosed systems and methods of the present invention generally relate to using an intracardiac electrogram (IEGM) and/or an electrocardiogram (ECG) to monitor a patient's venous blood oxygen saturation. While its possible and within the scope of the present invention to employ techniques of the present invention in an external (i.e., non-implantable) system, embodiments of the present invention are especially useful when employed by an implantable cardiac device. Accordingly, an exemplary implantable cardiac device in which embodiments of the present invention are useful is first described with reference to FIGS. 1 and 2.

Exemplary Implantable Device

Referring to FIG. 1, an exemplary implantable device 110 (also referred to as a pacing device, a pacing apparatus, a stimulation device, or simply a device) is in electrical communication with a patient's heart 112 by way of three leads, 120, 124 and 130, suitable for delivering multi-chamber stimulation. While not necessary to perform embodiments of the present invention, the exemplary device 110 is also capable of delivering shock therapy.

To sense atrial cardiac signals and to provide right atrial chamber stimulation therapy, the stimulation device 110 is coupled to an implantable right atrial lead 120 having at least an atrial tip electrode 122, which typically is implanted in the patient's right atrial appendage. To sense left atrial and ventricular cardiac signals and to provide left-chamber pacing therapy, the stimulation device 110 is coupled to a "coronary sinus" lead 124 designed for placement in the "coronary sinus region" via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 124 is designed to receive left atrial and ventricular cardiac signals and to deliver left atrial and ventricular pacing therapy using at least a left ventricular tip electrode 126, left atrial pacing therapy using at least a left atrial ring electrode 127, and shocking therapy using at least a left atrial coil electrode 128. The present invention may of course be practiced with a coronary sinus lead that does not include left atrial sensing, pacing or shocking electrodes.

The stimulation device 110 is also shown in electrical communication with the patient's heart 112 by way of an implantable right ventricular lead 130 having, in this embodiment, a right ventricular tip electrode 132, a right ventricular ring electrode 134, a right ventricular (RV) coil electrode 136, and an SVC coil electrode 138. Typically, the right ventricular lead 130 is transvenously inserted into the heart 112 so as to place the right ventricular tip electrode 132 in the right ventricular apex so that the RV coil electrode 136 will be positioned in the right ventricle and the SVC coil electrode 138 will be positioned in the superior vena cava. Accordingly, the right ventricular lead 130 is capable of receiving cardiac signals and delivering stimulation in the form of pacing and shock therapy to the right ventricle. It will be understood by those skilled in the art that other lead and electrode configurations such as epicardial leads and electrodes may be used in practicing the invention.

Figure 2:
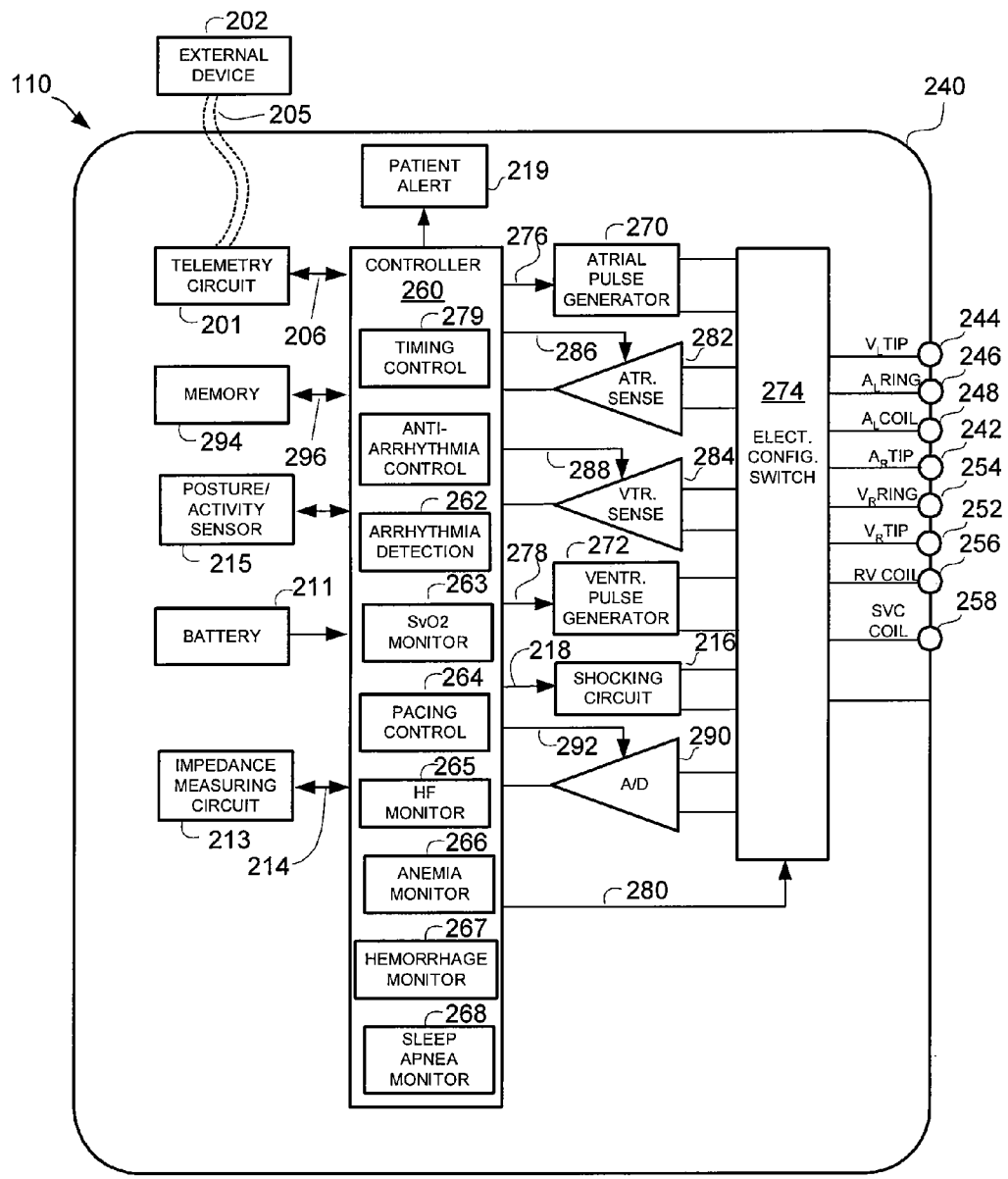
FIG. 2 is a functional block diagram of the multi-chamber implantable stimulation device of FIG. 1, illustrating the basic elements that provide pacing stimulation, cardioversion, and defibrillation in four chambers of the heart.

As illustrated in FIG. 2, a simplified block diagram is shown of the multi-chamber implantable implantable device 110, which is capable of treating both fast and slow arrhythmias with stimulation therapy, including pacing, cardioversion and defibrillation stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with pacing, cardioversion and defibrillation stimulation.

The housing 240 for the implantable device 110, shown schematically in FIG. 2, is often referred to as the "can", "case" or "case electrode" and may be programmably selected to act as the return electrode for all "unipolar" modes. The housing 240 may further be used as a return electrode alone or in combination with one or more of the coil electrodes, 128, 136 and 138, for shocking purposes. The housing 240 further includes a connector (not shown) having a plurality of terminals, 242, 244, 246, 248, 252, 254, 256, and 258 (shown schematically and, for convenience, the names of the electrodes to which they are connected are shown next to the terminals). As such, to achieve right atrial sensing and pacing, the connector includes at least a right atrial tip terminal ($A_R$ TIP) 242 adapted for connection to the atrial tip electrode 122.

To achieve left atrial and ventricular sensing, pacing and shocking, the connector includes at least a left ventricular tip terminal ($V_L$ TIP) 244, a left atrial ring terminal ($A_L$ RING) 246, and a left atrial shocking terminal ($A_L$ COIL) 148, which are adapted for connection to the left ventricular ring electrode 126, the left atrial tip electrode 127, and the left atrial coil electrode 128, respectively.

To support right ventricle sensing, pacing and shocking, the connector further includes a right ventricular tip terminal ($V_R$ TIP) 252, a right ventricular ring terminal ($V_R$ RING) 254, a right ventricular shocking terminal (Rv COIL) 256, and an SVC shocking terminal (SVC COIL) 258, which are adapted for connection to the right ventricular tip electrode 132, right ventricular ring electrode 134, the RV coil electrode 136, and the SVC coil electrode 138, respectively.

At the core of the implantable device 110 is a programmable microcontroller 260 which controls the various types and modes of stimulation therapy. As is well known in the art, the microcontroller 260 typically includes a microprocessor, or equivalent control circuitry, designed specifically for controlling the delivery of stimulation therapy and can further include RAM or ROM memory, logic and timing circuitry, state machine circuitry, and I/O circuitry. Typically, the microcontroller 260 includes the ability to process or monitor input signals (data) as controlled by a program code stored in a designated block of memory. The details of the design of the microcontroller 260 are not critical to the present invention. Rather, any suitable microcontroller 260 can be used to carry out the functions described herein. The use of microprocessor-based control circuits for performing timing and data analysis functions are well known in the art. In specific embodiments of the present invention, the microcontroller 260 performs some or all of the steps associated with arrhythmia detection.

Representative types of control circuitry that may be used with the invention include the microprocessor-based control system of U.S. Pat. No. 4,940,052 (Mann et. al.) and the state-machines of U.S. Pat. No. 4,712,555 (Sholder) and U.S. Pat. No. 4,944,298 (Sholder). For a more detailed description of the various timing intervals used within the pacing device and their inter-relationship, see U.S. Pat. No. 4,788,980 (Mann et. al.). The '052, '555, '298 and '980 patents are incorporated herein by reference.

An atrial pulse generator 270 and a ventricular pulse generator 272 generate pacing stimulation pulses for delivery by the right atrial lead 120, the right ventricular lead 130, and/or the coronary sinus lead 124 via an electrode configuration switch 274. It is understood that in order to provide stimulation therapy in each of the four chambers of the heart, the atrial and ventricular pulse generators, 270 and 272, may include dedicated, independent pulse generators, multiplexed pulse generators, or shared pulse generators. The pulse generators, 270 and 272, are controlled by the microcontroller 260 via appropriate control signals, 276 and 278, respectively, to trigger or inhibit the stimulation pulses.

The microcontroller 260 further includes timing control circuitry 279 which is used to control pacing parameters (e.g., the timing of stimulation pulses) as well as to keep track of the timing of refractory periods, noise detection windows, evoked response windows, alert intervals, marker channel timing, etc., which is well known in the art. Examples of pacing parameters include, but are not limited to, atrio-ventricular delay, interventricular delay and interatrial delay.

The switch bank 274 includes a plurality of switches for connecting the desired electrodes to the appropriate I/O circuits, thereby providing complete electrode programmability. Accordingly, the switch 274, in response to a control signal 280 from the microcontroller 260, determines the polarity of the stimulation pulses (e.g., unipolar, bipolar, etc.) by selectively closing the appropriate combination of switches (not shown) as is known in the art.

Atrial sensing circuits 282 and ventricular sensing circuits 284 may also be selectively coupled to the right atrial lead 120, coronary sinus lead 124, and the right ventricular lead 130, through the switch 274 for detecting the presence of cardiac activity in each of the four chambers of the heart. Accordingly, the atrial (ATR. SENSE) and ventricular (VTR. SENSE) sensing circuits, 282 and 284, may include dedicated sense amplifiers, multiplexed amplifiers, or shared amplifiers. The switch 274 determines the "sensing polarity" of the cardiac signal by selectively closing the appropriate switches, as is also known in the art. In this way, the clinician may program the sensing polarity independent of the stimulation polarity.

Each sensing circuit, 282 and 284, preferably employs one or more low power, precision amplifiers with programmable gain and/or automatic gain control, bandpass filtering, and a threshold detection circuit, as known in the art, to selectively sense the cardiac signal of interest. The automatic gain control enables the device 110 to deal effectively with the difficult problem of sensing the low amplitude signal characteristics of atrial or ventricular fibrillation. Such sensing circuits, 282 and 284, can be used to determine cardiac performance values used in the present invention. Alternatively, an automatic sensitivity control circuit may be used to effectively deal with signals of varying amplitude.

The outputs of the atrial and ventricular sensing circuits, 282 and 284, are connected to the microcontroller 260 which, in turn, are able to trigger or inhibit the atrial and ventricular pulse generators, 270 and 272, respectively, in a demand fashion in response to the absence or presence of cardiac activity, in the appropriate chambers of the heart. The sensing circuits, 282 and 284, in turn, receive control signals over signal lines, 286 and 288, from the microcontroller 260 for purposes of measuring cardiac performance at appropriate times, and for controlling the gain, threshold, polarization charge removal circuitry (not shown), and timing of any blocking circuitry (not shown) coupled to the inputs of the sensing circuits, 282 and 286. The sensing circuits can be used to acquire IEGM signals, which can be used for monitoring levels of SvO2 in according with embodiments of the present invention. Where the implantable system include subcutaneous electrodes, the sensing circuits can be used to acquire ECG signals, which can be used for monitoring levels of SvO2 in accordance with embodiments of the present invention.

For arrhythmia detection, the device 110 includes an arrhythmia detector 262 that utilizes the atrial and ventricular sensing circuits, 282 and 284, to sense cardiac signals to determine whether a rhythm is physiologic or pathologic. The timing intervals between sensed events (e.g., P-waves, R-waves, and depolarization signals associated with fibrillation) are then classified by the microcontroller 260 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to assist with determining the type of remedial therapy that is needed (e.g., bradycardia pacing, anti-tachycardia pacing, cardioversion shocks or defibrillation shocks, collectively referred to as "tiered therapy"). The arrhythmia detector 262 can be implemented within the microcontroller 260, as shown in FIG. 2. Thus, this detector 262 can be implemented by software, firmware, or combinations thereof. It is also possible that all, or portions, of the arrhythmia detector 262 can be implemented using hardware. Further, it is also possible that all, or portions, of the arrhythmia detector 262 can be implemented separate from the microcontroller 260.

In accordance with embodiments of the present invention, the implantable device 110 also includes an SvO2 monitor 263, that monitors a patient's venous oxygen saturation level using embodiments of the present invention, which are described in detail below with reference to FIGS. 4-12. The SvO2 monitor 263 can be implemented within the microcontroller 260, as shown in FIG. 2. Thus, the SvO2 monitor 263 can be implemented by software, firmware, or combinations thereof. It is also possible that all, or portions, of the monitor 263 can be implemented using hardware. Further, it is also possible that all, or portions, of the monitor 263 can be implemented separate from the microcontroller 260. The SvO2 monitor can include, or communicate with, a component that measures metrics of the IEGM and/or ECG signals.

The implantable device 110 is also shown as including a pacing controller 264, which can adjust a pacing rate and/or pacing intervals based on measures of SvO2, in accordance with embodiments of the present invention described below. Additionally, the implantable device is shown as including a heart failure (HF) monitor 265, an anemia monitor 266, a hemorrhaging monitor 267, and a sleep apnea monitor 268. The HF monitor 265 can monitor a patient's HF condition based on measures of SvO2, in accordance with embodiments of the present invention described below. The hemorrhaging monitor 267 can monitor for internal hemorrhaging, in accordance with embodiments of the present invention described below. The sleep apnea monitor 268 can monitor for episodes of sleep apnea, in accordance with embodiments of the present invention described below.

The pacing controller 264 and the monitors 265, 266, 267 and 268 can be implemented within the microcontroller 260, as shown in FIG. 2. Thus, the monitors can be implemented by software, firmware, or combinations thereof. It is also possible that all, or portions, of the pacing controller 264 and monitors 265, 266, 267 and 268 can be implemented using hardware. Further, it is also possible that all, or portions, of the pacing controller 264 and monitors 265, 266, 267 and 268 can be implemented separate from the microcontroller 260. The pacing controller 264 and monitors 265, 266, 267 and 268 can communicate with the SvO2 monitor 263, or each such controller or monitor can monitor levels of SvO2 on their own.

The implantable device 110 is also shown as including a posture and/or activity sensor 215, which can detect a patient's posture and/or level of activity. The sensor 215 can be, e.g., a DC-coupled 3-dimensional accelerometer as described in U.S. Pat. No. 6,658,292, a multi-axis DC accelerometer as described in U.S. Pat. No. 6,466,821, or an external field sensor as described in U.S. Pat. No. 6,625,493, each of which are incorporated herein by reference. Such sensors are able to distinguish among different static positions. In addition, since the sensors can detect motion, they can be used to distinguish between a static vertical position, such as sitting, and a standing position, which due to the dynamics of balance is associated with subtle motion that is not present while sitting. In this way an implantable device, using one of the above mentioned sensors or other sensing modality, can detect whether it is likely that a patient is sleeping, e.g., if the patient is detected to be supine and inactive.

Still referring to FIG. 2, cardiac signals are also applied to the inputs of an analog-to-digital (A/D) data acquisition system 290. The data acquisition system 290 is configured to acquire intracardiac electrogram signals, convert the raw analog data into a digital signal, and store the digital signals for later processing and/or telemetric transmission to an external device 202. The data acquisition system 290 is coupled to the right atrial lead 120, the coronary sinus lead 124, and the right ventricular lead 130 through the switch 274 to sample cardiac signals across any pair of desired electrodes.

The data acquisition system 290 can be coupled to the microcontroller 260, or other detection circuitry, for detecting an evoked response from the heart 112 in response to an applied stimulus, thereby aiding in the detection of "capture". Capture occurs when an electrical stimulus applied to the heart is of sufficient energy to depolarize the cardiac tissue, thereby causing the heart muscle to contract. The microcontroller 260 detects a depolarization signal during a window following a stimulation pulse, the presence of which indicates that capture has occurred. The microcontroller 260 enables capture detection by triggering the ventricular pulse generator 272 to generate a stimulation pulse, starting a capture detection window using the timing control circuitry 279 within the microcontroller 260, and enabling the data acquisition system 290 via control signal 292 to sample the cardiac signal that falls in the capture detection window and, based on the amplitude, determines if capture has occurred.

The implementation of capture detection circuitry and algorithms are well known. See for example, U.S. Pat. No. 4,729,376 (Decote, Jr.); U.S. Pat. No. 4,708,142 (Decote, Jr.); U.S. Pat. No. 4,686,988 (Sholder); U.S. Pat. No. 4,969,467 (Callaghan et. al.); and U.S. Pat. No. 5,350,410 (Mann et. al.), which patents are hereby incorporated herein by reference. The type of capture detection system used is not critical to the present invention.

The microcontroller 260 is further coupled to the memory 294 by a suitable data/address bus 296, wherein the programmable operating parameters used by the microcontroller 260 are stored and modified, as required, in order to customize the operation of the implantable device 110 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 112 within each respective tier of therapy. The memory 294 can also be used to store information about various episodes, occurrences and changes in conditions that are detected using embodiments of the present invention.

The operating parameters of the implantable device 110 may be non-invasively programmed into the memory 294 through a telemetry circuit 201 in telemetric communication with an external device 202, such as a programmer, transtelephonic transceiver, or a diagnostic system analyzer. The telemetry circuit 201 can be activated by the microcontroller 260 by a control signal 206. The telemetry circuit 201 advantageously allows intracardiac electrograms and status information relating to the operation of the device 110 (as contained in the microcontroller 260 or memory 294) to be sent to the external device 202 through an established communication link 204. The telemetry circuit 201 can also be used to trigger alarms or alerts of the external device 202, or to instruct the external device 202 to notify a caregiver regarding detection of various episodes, occurrences and changes in conditions that are detected using embodiments of the present invention.

For examples of such devices, see U.S. Pat. No. 4,809,697, entitled "Interactive Programming and Diagnostic System for use with Implantable Pacemaker" (Causey, III. et al.); U.S. Pat. No. 4,944,299, entitled "High Speed Digital Telemetry System for Implantable Device" (Silvian); and U.S. Pat. No. 6,275,734 entitled "Efficient Generation of Sensing Signals in an Implantable Medical Device such as a Pacemaker or ICD" (McClure et al.), which patents are hereby incorporated herein by reference.

The implantable device 110 additionally includes a battery 211 which provides operating power to all of the circuits shown in FIG. 2. If the implantable device 110 also employs shocking therapy, the battery 211 should be capable of operating at low current drains for long periods of time, and then be capable of providing high-current pulses (for capacitor charging) when the patient requires a shock pulse. The battery 211 should also have a predictable discharge characteristic so that elective replacement time can be detected.

The implantable device 110 can also include a magnet detection circuitry (not shown), coupled to the microcontroller 260. It is the purpose of the magnet detection circuitry to detect when a magnet is placed over the implantable device 110, which magnet may be used by a clinician to perform various test functions of the implantable device 110 and/or to signal the microcontroller 260 that the external programmer 202 is in place to receive or transmit data to the microcontroller 260 through the telemetry circuits 201.

As further shown in FIG. 2, the device 110 is also shown as having an impedance measuring circuit 213 which is enabled by the microcontroller 260 via a control signal 214. The known uses for an impedance measuring circuit 213 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds and heart failure condition; detecting when the device has been implanted; measuring stroke volume; and detecting the opening of heart valves, etc. The impedance measuring circuit 213 is advantageously coupled to the switch 274 so that any desired electrode may be used. The impedance measuring circuit 213 is not critical to the present invention and is shown only for completeness.

In the case where the implantable device 110 is also intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 260 further controls a shocking circuit 216 by way of a control signal 218. The shocking circuit 216 generates shocking pulses of low (up to 0.5 Joules), moderate (0.5-10 Joules), or high energy (11 to 40 Joules), as controlled by the microcontroller 260. Such shocking pulses are applied to the patient's heart 112 through at least two shocking electrodes, and as shown in this embodiment, selected from the left atrial coil electrode 228, the RV coil electrode 236, and/or the SVC coil electrode 238. As noted above, the housing 240 may act as an active electrode in combination with the RV electrode 236, or as part of a split electrical vector using the SVC coil electrode 238 or the left atrial coil electrode 228 (i.e., using the RV electrode as a common electrode).

The above described implantable device 110 was described as an exemplary pacing device. One or ordinary skill in the art would understand that embodiments of the present invention can be used with alternative types of implantable devices. Accordingly, embodiments of the present invention should not be limited to use only with the above described device.

Exemplary External Device

Figure 3:
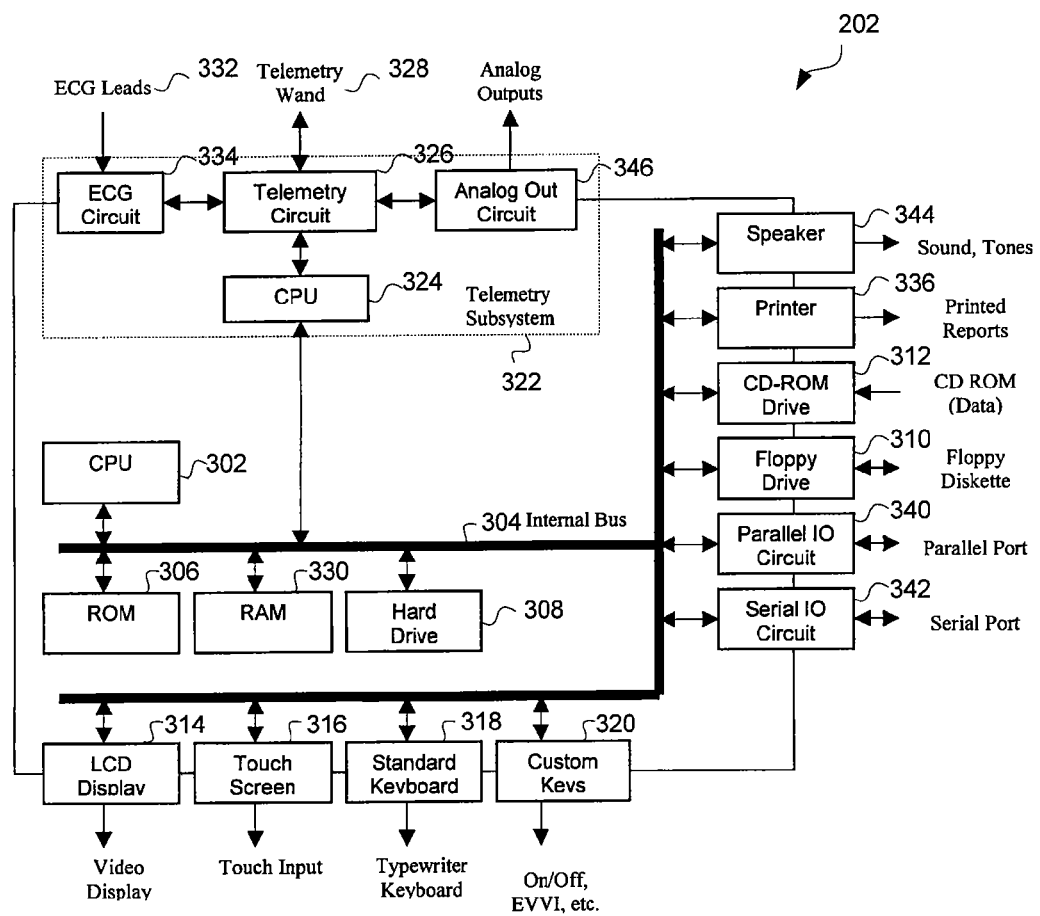
FIG. 3 is a functional block diagram of an exemplary external programmer.

FIG. 3 will now be used to illustrate components of an exemplary external programmer 202 for use in programming the implantable device 110, uploading data from the implantable device, and analyzing such data. Briefly, the programmer permits a physician or other user to program the operation of the implantable device 110 and to retrieve and display information received from the implantable device such as IEGM data and device diagnostic data. Additionally, the external programmer can receive and display ECG data from separate external ECG leads that may be attached to the patient. As will be described in further detail below, in accordance with embodiments of the present invention, the external programmer 202 is capable of processing and analyzing data received from the implantable device 110.

Operations of the programmer 202 are controlled by a CPU 302, which may be a generally programmable microprocessor or microcontroller or may be a dedicated processing device such as an application specific integrated circuit (ASIC) or the like. Software instructions to be performed by the CPU are accessed via an internal bus 304 from a read only memory (ROM) 306 and random access memory 330. Additional software may be accessed from a hard drive 308, floppy drive 310, and CD ROM drive 312, or other suitable permanent mass storage device. Depending upon the specific implementation, a basic input output system (BIOS) is retrieved from the ROM by CPU at power up. Based upon instructions provided in the BIOS, the CPU "boots up" the overall system in accordance with well-established computer processing techniques.

Once operating, the CPU 302 displays a menu of programming options to the user via an LCD display 314 or other suitable computer display device. To this end, the CPU may, for example, display a menu of specific programming parameters of the implantable device to be programmed or may display a menu of types of diagnostic data to be retrieved and displayed. In response thereto, the physician enters various commands via either a touch screen 316 overlaid on the LCD display or through a standard keyboard 318 supplemented by additional custom keys 320, such as an emergency VVI (EVVI) key. The EVVI key sets the implantable device to a safe VVI mode with high pacing outputs. This ensures life sustaining pacing operation in nearly all situations but by no means is it desirable to leave the implantable device in the EVVI mode at all times.

Once all pacing leads are mounted and the implantable device 110 is implanted, the various devices are programmed. Typically, the physician initially controls the programmer 202 to retrieve data stored within any implantable device 110 and to also retrieve ECG data from ECG leads 332, if any, coupled to the patient. To this end, the CPU 302 transmits appropriate signals to a telemetry subsystem 322, which provides components for directly interfacing with the implantable device 110, and the ECG leads. Telemetry subsystem 322 includes its own separate CPU 324 for coordinating the operations of the telemetry subsystem. Main CPU 302 of programmer communicates with telemetry subsystem CPU 324 via internal bus 304. Telemetry subsystem 322 additionally includes a telemetry circuit 326 connected to telemetry wand 328, which, in turn, receives and transmits signals electromagnetically from the telemetry unit 201 of the implantable device 110. The telemetry wand 328 is placed over the chest of the patient near the implantable device to permit reliable transmission of data between the telemetry wand 328 and the implantable device 110.

Typically, at the beginning of the programming session, the external programming device 202 controls the implantable device 110 via appropriate signals generated by the telemetry wand 328 to output all previously recorded patient and device diagnostic information. Patient diagnostic information includes, for example, recorded IEGM data and statistical patient data such as the percentage of paced versus sensed heartbeats. Device diagnostic data includes, for example, information representative of the operation of the implantable device such as lead impedances, battery voltages, battery recommended replacement time (RRT) information and the like. Data retrieved from the implantable device 110 is stored by external programmer 202 either within a random access memory (RAM) 330, hard drive 308 or within a floppy diskette placed within floppy drive 310. Additionally, or in the alternative, data may be permanently or semi-permanently stored within a compact disk (CD) or other digital media disk, if the overall system is configured with a drive for recording data onto digital media disks, such as a write once read many (WORM) drive.

Once all patient and device diagnostic data previously stored within the implantable device 110 is transferred to programmer 202, the implantable device 110 may be further controlled to transmit additional data in real time as it is detected by the implantable device 110, such as additional IEGM data, lead impedance data, and the like. Additionally, or in the alternative, telemetry subsystem 322 receives ECG signals from ECG leads 332 via an ECG processing circuit 334. As with data retrieved from the implantable device itself, signals received from the ECG leads are stored within one or more of the storage devices of the external programmer. Typically, ECG leads output analog electrical signals representative of the ECG. Accordingly, ECG circuit 334 includes analog to digital conversion circuitry for converting the signals to digital data appropriate for further processing within programmer. Depending upon the implementation, the ECG circuit 334 may be configured to convert the analog signals into event record data for ease of processing along with the event record data retrieved from the implantable device. Typically, signals received from the ECG leads are received and processed in real time.

Thus, the programmer 202 can receive data both from the implantable device 110 and from the external ECG leads 332. In specific embodiments of the present invention the programmer 202 receives IEGM signals from the implantable device 110 and/or ECG signals from the implantable device 110, or from the ECG processing circuit 334, the programmer 202 monitors SvO2 using techniques of the present invention described below.

Data retrieved from the implantable device 110 includes parameters representative of the current programming state of the implantable device 110. Under the control of the physician, the external programmer 202 displays the current programming parameters and permits the physician to reprogram the parameters. To this end, the physician enters appropriate commands via any of the aforementioned input devices and, under control of CPU 302, the programming commands are converted to specific programming parameters for transmission to the implantable device 110 via telemetry wand 328 to thereby reprogram the implantable device 110. A wide variety of parameters may be programmed by the physician, including, but not limited to atrioventricular and inter-ventricular delay values. Prior to reprogramming specific parameters, the physician may control the external programmer 202 to display any or all of the data retrieved from the implantable device 110 or from the ECG leads, including displays of ECGs, IEGMs, and statistical patient information. Any or all of the information displayed by programmer may also be printed using a printer 336.

The programmer 202 also includes a modem 338 to permit direct transmission of data to other programmers via the public switched telephone network (PSTN) or other interconnection line, such as a T1 line or fiber optic cable. Depending upon the implementation, the modem may be connected directly to internal bus 304 may be connected to the internal bus via either a parallel port 340 or a serial port 342. Other peripheral devices may be connected to the external programmer via parallel port 340 or a serial port 342 as well. Although one of each is shown, a plurality of input output (10) ports might be provided. A speaker 344 is included for providing audible tones to the user, such as a warning beep in the event improper input is provided by the physician. The telemetry subsystem 322 additionally includes an analog output circuit 346 for controlling the transmission of analog output signals, such as IEGM signals output to an ECG machine or chart recorder.

With the programmer 202 configured as shown, a physician or other user operating the external programmer is capable of retrieving, processing and displaying a wide range of information received from the ECG leads or from the implantable device 110 and to reprogram the implantable device 110 if needed. The descriptions provided herein with respect to FIG. 3 are intended merely to provide an overview of the operation of an exemplary external programmer 202 and are not intended to describe in detail every feature of the hardware and software of the device and is not intended to provide an exhaustive list of the functions performed by the device.

Preferred Embodiments

Figure 4:
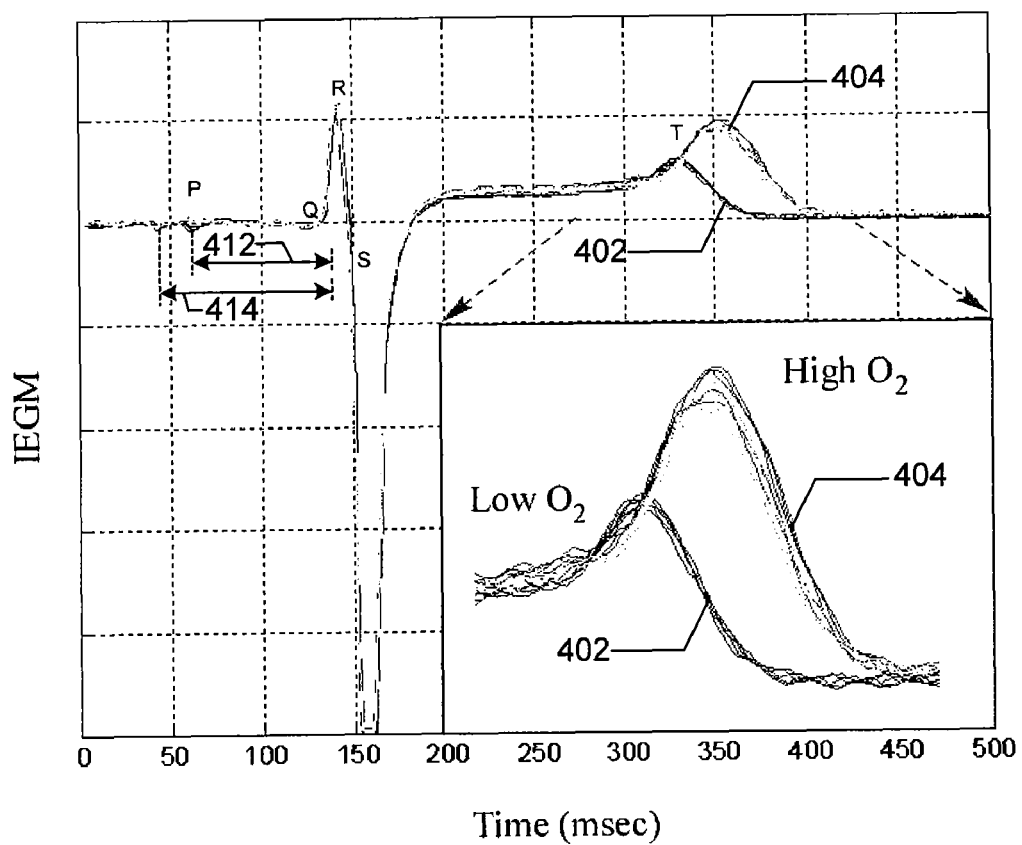
FIG. 4 show two IEGMs obtained at two different times, but which have been overlayed on top of one another, to illustrate how venous blood oxygen saturation (SvO2) can be monitored based on IEGMs, in accordance with embodiments of the present invention.

The inventors of the present invention have discovered that changes in venous blood oxygen saturation (SvO2) affects the repolarization wave (T-wave) of IEGMs signals and ECGs. FIG. 4 illustrates this phenomena. Shown in FIG. 4 is a first IEGM 402 and a second IEGM 404, which were obtained at two different times, but which have been overlayed on top of one another. At the same times that the IEGMs 402 and 404 were obtained, the patient's venous blood oxygen saturation (SvO2) was also measured using an external oximeter attached to an implanted catheter inserted into the pulmonary artery, with the oximeter being an Oximetrics's OSM3 model. When comparing the two IEGMs 402 and 404, along with the corresponding SvO2 values, it was discovered that that the repolarization wave (T-wave) was markedly larger when the oxygen saturation was higher. Additionally, it was discovered that the QT interval was significantly longer when venous oxygen saturation was higher. Based on this, the inventors realized that changes in venous oxygen saturation can be monitored based on changes in T-wave metrics of IEGMs and/or ECGs.

The PR interval is the time from the beginning of the P-wave (indicative of onset of atrial depolarization) to the beginning of the QRS complex (indicative of onset of ventricular depolarization). The inventors of the present invention have also realized that PR intervals vary with varying levels of SvO2. Referring again to FIG. 4, PR interval 412 of IEGM 402 and PR interval 414 of IEGM 404 are shown. As was mentioned above, at the time IEGM 404 was obtained, the patient's SvO2 was higher than at the time IEGM 402 was obtained. Accordingly, it can be appreciated from FIG. 4 that a patient's PR interval increases with SvO2, and vice versa.

Articles have been published that discussed alleged correlations between various blood oxygen levels and T-wave amplitudes. For example, an article by Kayer et al entitled "Relationship between T-wave amplitude and oxygen pulse in guinea pigs in hyperbaric helium and hydrogen" J Applied Physiology, 85 (3), 798-806, 1998, concluded that the amplitude of the T-wave correlates with the total volume of O2 consumed by an animal per heart beat (known as O2 pulse). More specifically, the Kayer et al article concluded that O2 pulse increased with increasing T-wave amplitude.

The Kayer et al article does not discuss any relationship between T-wave amplitudes and SvO2. However, it is known that oxygen consumption (O2 consumed) can be determined by subtracting SvO2 from arterial oxygen saturation (SaO2). In other words, O2 consumed=SaO2−SvO2. It is also known that SaO2 stays generally constant in patients having normal lung function. Thus, it is known that O2 consumed has an inverse correlation with SvO2. In other words, it is known that a decrease in SvO2 is generally indicative of an increase in oxygen consumption.

The Kayer et al article discussed above concluded that oxygen consumption increased with increasing T-wave amplitude. Knowing that a decrease in SvO2 is generally indicative of an increase in oxygen consumption, the Kayer et al article would lead one to believe that an increase in T-wave amplitude (which according to Kayer et al. is indicative of an increase on O2 consumed) is indicative of a decrease in SvO2, and vice versa. However, that is exactly the opposite of what the inventors of the present invention have discovered. Thus, it is clear that the Kayer et al article teaches away from the present invention.

Another article, by Penneys et al, which is entitled "The Relationship between the Arterial Oxygen Saturation and the Cardiovascular Response to Induced Anoxemia in Normal Young Adults" Circulation, 1950; 1; 415-425, concluded that the T-wave was progressively lowered with diminishing arterial oxygen saturation, and that the degree of lowering was closely correlated with the level of arterial oxygen saturation. This article, however, did not address oxygen consumption or SvO2. Stating that arterial oxygen saturation (SaO2) lowers with a lower T-wave says nothing to what happens to the SvO2, since SvO2 is a function of both SaO2 and oxygen consumption. In other words, a decrease in SaO2 can coincide with either a decrease or an increase in SvO2, depending on the oxygen consumption. Further, as mentioned above, SaO2 generally stays the same in patients having normal lung function. In contrast, SvO2 can have significant variation in patients having normal lung function. Thus, the Penneys et al article is not believed to provide any insight into how changes in T-waves affect SvO2.

Flowcharts

Figure 5:
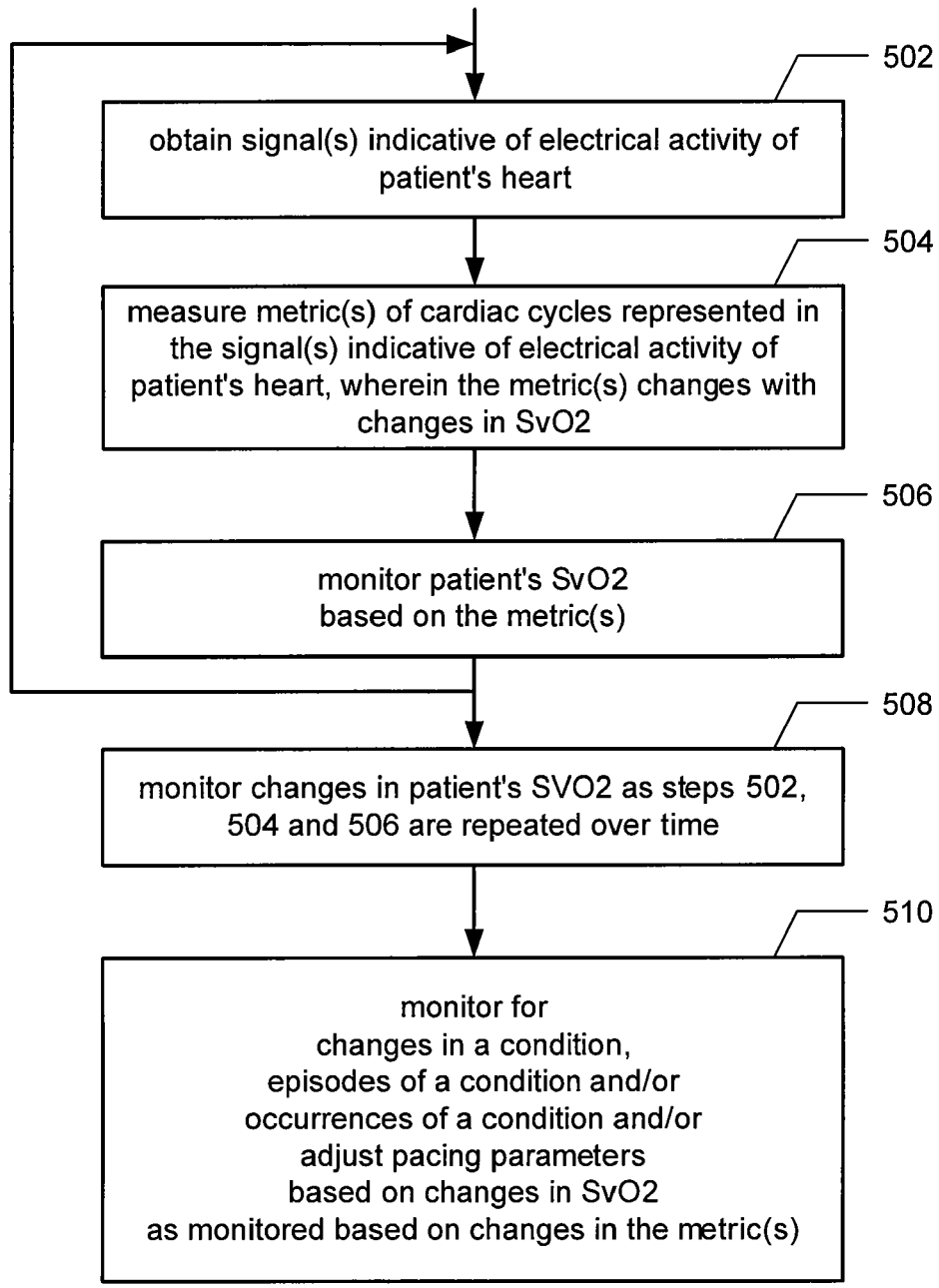
FIG. 5 is a high level flow diagram that is used to summarize various embodiments of the present invention in which a patient's SvO2 is monitored based on a signal (e.g., IEGM) indicative of electrical activity of the patient's heart.

FIG. 5 is a high level flow diagram that is used to summarize specific embodiments of the present invention. More specifically, the flow chart of FIG. 5 is used to summarize specific embodiments for monitoring a patient's venous blood oxygen saturation (SvO2), in accordance with specific embodiments of the present invention. In this flow diagram, and other flow diagrams presented herein, the various algorithmic steps are summarized in individual "blocks". Such blocks describe specific actions or decisions that are made or carried out as the algorithm proceeds. Where a microcontroller (or equivalent) is employed, the flow diagrams presented herein provide the basis for a "control program" that may be used by such a microcontroller (or equivalent) to effectuate the desired control of an implantable device and/or an external device. Those skilled in the art may readily write such a control program based on the flow diagrams and other descriptions presented herein.

Referring to FIG. 5, at step 502, at least one signal indicative of electrical activity of a patient's heart is obtained. A signal indicative of electrical activity of a patient's heart can be an intracardiac electrogram (IEGM), obtained using implanted cardiac electrodes, examples of which were described above with reference to FIGS. 1 and 2. Alternatively, or additionally, a signal indicative of electrical activity of a patient's heart can be an electrocardiogram (ECG). An ECG can be obtained using implanted subcutaneous electrodes. Alternative, an ECG can be obtained using non-implanted electrodes, e.g., attached to a patient's chest.

At step 504, there is a measurement of at least one metric of cardiac cycles represented in the obtained signal (indicative of electrical activity of the patient's heart), wherein the at least one metric changes with changes in SvO2. For reasons explained above with reference to FIG. 4, the metric(s) measured at step 504 can be one or more T-wave metric. Exemplary T-wave metrics that may change with changes in SvO2 include T-wave amplitude maximum, T-wave amplitude minimum, T-wave amplitude peak-to-peak, T-wave amplitude dispersion, T-wave centroid, QT interval, T-wave area, T-wave frequency content and T-wave frequency spread. Another exemplary T-wave metric, that may change with changes in SvO2, is T-wave slope. Such T-wave metrics can be corrected for heart rate, because certain T-wave metrics will vary with heart rate, even where the SvO2 remains constant. For example, QT intervals will normally decrease with increases in heart rate (which can be measured by measuring the RR interval), and QT intervals will normally increase with decreases in heart rate (i.e., increases in RR interval). However, for a given heart rate/RR interval, it is believed that the QT interval will increase as SvO2 increases, and vise versa, as can be appreciated from FIG. 4. Thus, it would be appropriate to correct or adjust (or otherwise normalize) a measures of QT intervals, as well as other T-wave metrics. Exemplary equations for normalizing a QT interval can involve dividing the measured QT interval by the square root of the corresponding RR interval, or dividing the measured QT interval by $RR^{(1/3)}$. These are just a few examples, which are not meant to be limiting.

Other T-wave metrics can also be normalized. Such normalization can be, e.g., to compensate for changes in the signal obtained at step 502 that are due to enlargement of the heart due to hypertrophic cardiomyopathy. For example, as the heart enlarges, the amplitude of the T-wave may increase due to the enlargement. However, the R-wave should also increase when the heart enlarges. By producing a ratio of T-wave amplitude to R-wave amplitude (at step 504), a relative change in the T-wave amplitude can be measured, to thereby monitor levels of and changes in SvO2 (at steps 506 and 508). This is just one example of how features of the signal obtained at step 502 can be used to normalize a T-wave metric. Additional and alternative features of the signal obtained at step 502 can also be used to normalize T-wave metrics. In accordance with specific embodiments, pacing mode normalization is performed. The T-wave morphology is different in a paced cardiac cycle than an intrinsic cardiac cycle. The ICD microcontroller determines if the heart needs to be paced. In the instances in which the heart is paced, the T-wave metric recorded can be normalized such that it is comparable to an intrinsic T wave metric. Alternatively, pacing mode normalization can be accomplished by only recording the T-wave metrics during the patient's dominate rhythm type.

Figure 12:
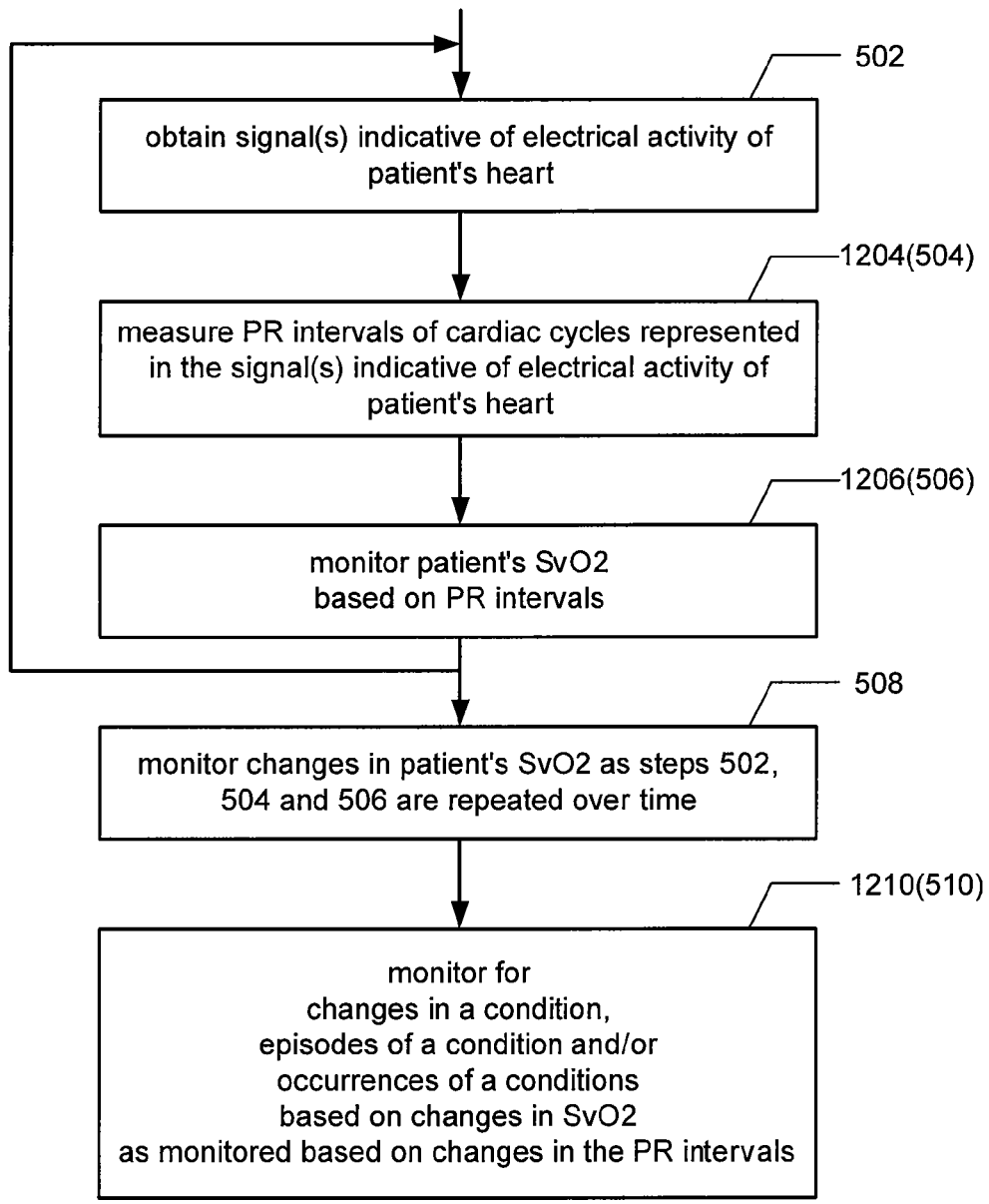
FIG. 12 is a high level flow diagram that is used to explain that a metric used to monitor SvO2 can be PR intervals.

An alternative or additional metric that can be measured at step 504 is PR interval. As was explained above with reference to FIG. 4, it is expected that PR intervals will increase with increases SvO2, and vice versa. FIG. 12, described below, provides some additional details of the use of PR intervals. For similar reasons discussed above, PR intervals should also be normalized, because PR intervals also normally change with changes in heart rate.

A single measure of a specific metric (e.g., T-wave peak-to-peak amplitude) can be measured for a single cardiac cycle at step 504. Alternatively, the metric (e.g., T-wave peak-to-peak amplitude) can be measured for a predetermined plurality of cardiac intervals, and the measured metrics can be averages, summed, or otherwise combined into a single measurement that is stored and used in further steps. A single type of metric can be measured at step 504 (e.g., T-wave amplitude peak-to-peak), or multiple types of metrics can be measured at step 504 (e.g., T-wave amplitude peak-to-peak, QT interval and PR interval).

At step 506, the patient's SvO2 is monitored based on the metric(s) measured at step 504. In certain embodiments, relative levels of SvO2 can be determined at step 506, e.g., by comparing the metrics obtained at step 504 to previously obtained metrics and/or thresholds. It is also possible to calibrate various metrics to actual measures of SvO2, during a calibration procedure, so that more specific measures of SvO2 (e.g., relatively absolute measures of SvO2) can be obtained at step 506.

As shown at 508, steps 502, 504 and 506 can be repeated over time so that changes in SvO2 can be monitored. For example, steps 502, 504 and 506 can be performed continuously, periodically (e.g., every minute, hour, day, etc.), or aperiodically (e.g., in response to specific triggering events). In accordance with specific embodiments, data indicative of the metrics measured at steps 502 and/or levels of SvO2 as determined at step 504, are saved for later analysis and/or trending. Such data can be stored, e.g., in memory 294 of device 110.

In accordance with specific embodiments, at step 508, increases in a T-wave metric can be interpreted as increases in the patient's SvO2, and decreases in a T-wave metric can be interpreted as decreases in the patient's SvO2. For example, an increase in peak-to-peak T-wave amplitude can be interpreted as in increase in SvO2, and a decrease in peak-to-peak T-wave amplitude can be interpreted as a decrease in SvO2. Similarly, where PR interval is a measured metric, increases in PR interval can be interpreted as increases in the patient's SvO2, and decreases in PR interval can be interpreted as decreases in the patient's SvO2.

It is noted that if T-wave minimum is used as a metric, whether increases or decreases in the T-wave minimum are indicative of increases in SvO2 depends on how the T-wave minimum is measured. For example, if T-wave minimum is a measurement of the amount the T-wave deviates below the relatively constant plateau between the QRS complex and the T-wave, then it is expected that increases in T-wave minimum are indicative of increases in SvO2, and vice versa. However, if T-wave minimum is a measurement of the amplitude at the low point of the T-wave, relative to a zero X-axis, then it is expected that decreases in T-wave minimum are indicative of increases in SvO2, and vice versa. Further, it is noted that the hardware used to obtain the signals shown in FIG. 4 essentially filtered out deviations in the T-wave minimum. However, when alternative types of hardware are used, changes in the T-wave minimum can be more readily apparent and measured.

Figure 6:
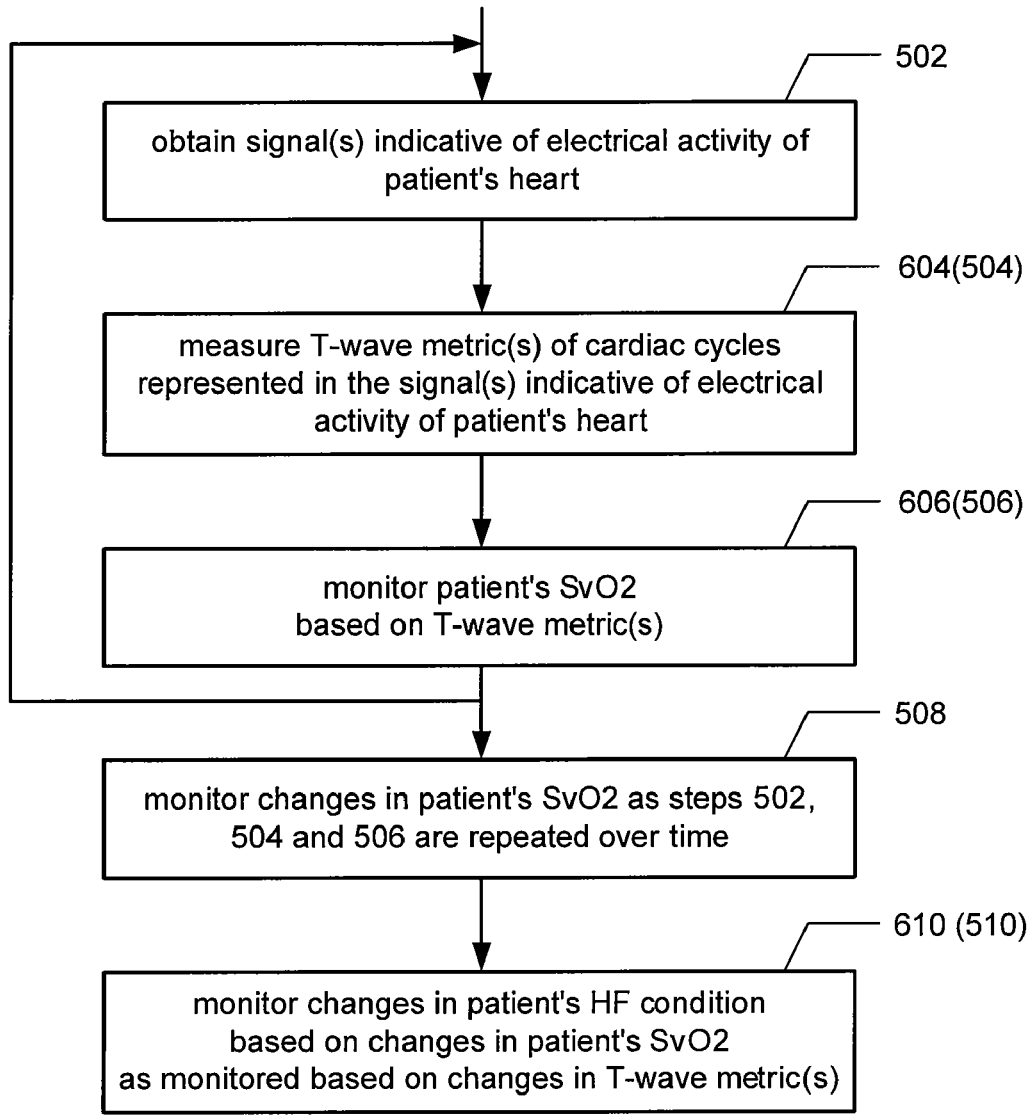
FIG. 6 is a high level flow diagram that is used to summarize how a patient's SvO2 can be monitored based on T-wave metrics, and that the monitored SvO2 can be used to monitor a patient's heart failure condition.

At step 510, various conditions, episodes of conditions and/or occurrences of conditions can be monitored for based on the changes in SvO2, as monitored based on changes in the measured metric(s) of an IEGM and/or ECG. Additionally, or alternatively, pacing parameters can be adjusted at step 510. Additional details of step 510 will be discussed with below reference to FIGS. 6-11. More specifically, FIGS. 6-11 are flow diagrams that provide additional details of many of the steps introduced in FIG. 5. In each of these FIGS., where a reference number is shown adjacent another reference number that is in parentheses, the step identified by the reference number is a specific embodiment of the step identified by the reference number in parenthesis. For example, in FIG. 6, where a step is identified as "604 (504)", this means that step 604 introduced in FIG. 6 is a specific embodiment of the step 504 previously introduced in FIG. 5. Where a step in FIGS. 6-11 is identified with a reference number introduced and discussed earlier. i.e., with reference to an earlier FIG., then that step is the same as the step discussed with reference to the earlier FIG. For example, step 502 in FIGS. 6-12 is the same as step 502 in FIG. 5, and thus, that step need not be discussed in detail repeatedly. Rather, the reader should reference the discussion of the earlier FIG.

Referring now to FIG. 6. At step 502, one or more signal indicative of electrical activity of a patient's heart is obtained, as was explained above with reference to FIG. 5.

At step 604, which is a specific embodiment of step 504, at least one T-wave metric is measured. Exemplary T-wave metrics that can be measured were discussed above with reference to FIGS. 5 and 4.

At step 606, a patient's SvO2 is monitored based on the T-wave metric(s) measured at step 604. In certain embodiments, relative levels of SvO2 can be determined at steps 606, e.g., by comparing the T-wave metric(s) obtained at step 604 to previously obtained T-wave metrics and/or corresponding T-wave metric thresholds. It is also possible to calibrate various T-metrics to actual measures of SvO2, during a calibration procedure, so that more specific measures of SvO2 (e.g., relatively absolute measures of SvO2) can be obtained at step 606.

As specified at 608, changes in the patient's SvO2 are monitored as steps 602, 604 and 606 are repeated over time. As was explained above, in accordance with specific embodiments, increases in the T-wave metric(s) are interpreted as increases in the patient's SvO2, and decreases in the T-wave metric(s) are interpreted as decreases in the patient's SvO2.

At step 610, which is a specific embodiment of step 510, changes in the patient's heart failure (HF) condition are monitored based on changes in the patient's SvO2, as monitored based on changes in T-wave metric(s). In specific embodiments, step 610 includes interpreting decreases in the patient's SvO2 over time as being indicative of worsening of the patient's HF, and interpreting increases in the patient's SvO2 over time as being indicative of improvement of the patient's HF. When an HF condition reaches a specific level, a patient and/or physician can be alerted.

Figure 7:
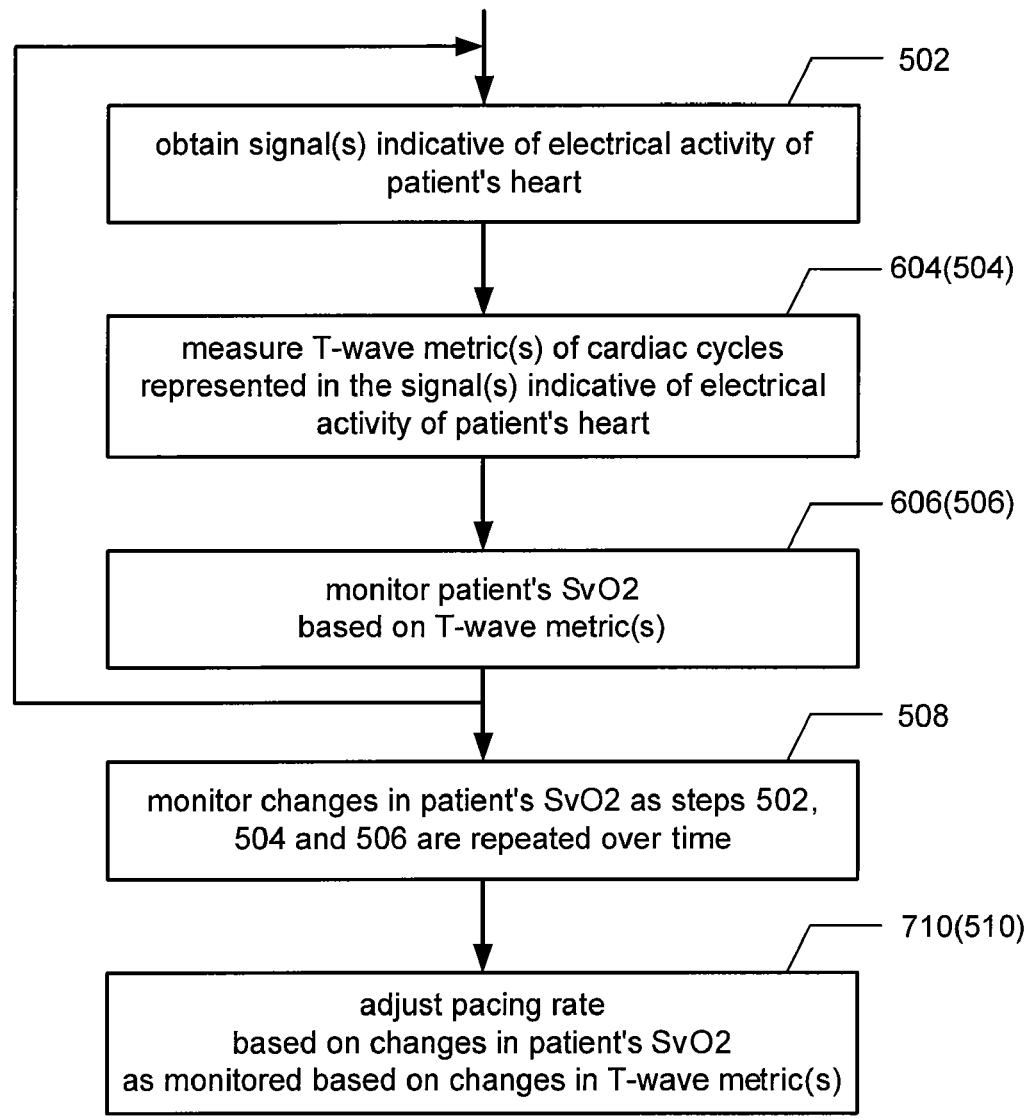
FIG. 7 is a high level flow diagram that is used to summarize how pacing rates can be adjusted in accordance with embodiments of the present invention.

The flow diagram of FIG. 7 explains how embodiments of the present invention can be used to adjust a pacing rate. The flow diagram of FIG. 8 explains how embodiments of the present invention can be used to adjust pacing intervals. The flow diagram of FIG. 9 explains how embodiments of the present invention can be used to monitor for anemic episodes. The flow diagram of FIG. 10 explains how embodiments of the present invention can be used to monitor for internal hemorrhaging. The flow diagram of FIG. 11 explain how embodiment of the present invention can be used to monitor for episodes of sleep apnea. As can be seen from FIGS. 7-11, all of the steps of FIGS. 7-11, except the last step in each FIG., are the same as the steps of FIG. 6. Accordingly, when discussing FIGS. 7-11, only the last step shown in each FIG. need be discussed. For additional details of the other steps of FIGS. 7-11, reference should be made to the discussion above.

Referring now to FIG. 7, at step 710, which is a specific embodiment of step 510, a pacing rate is adjusted based on changes in SvO2, as monitored based on changes in measured T-wave metric(s). This can include adjusting the pacing rate to attempt to maintain the patient's SvO2 at a specified level. The specified level can be an optimal level, e.g., as specified by a physician. Alternatively, the specified level can be a maximum SvO2 level. In specific embodiments, step 710 includes increasing the pacing rate to attempt to increase the patient's SvO2. Step 710 can also include decreasing the pacing rate to attempt to reduce the patient's SvO2. In some patients, it may be that pacing beyond a certain rate will start to decrease the patient's SvO2. Accordingly, it's also possible that step 710 can include decreasing the patient's pacing rate to attempt to increase the patient's SvO2, and vice versa.

Figure 8:
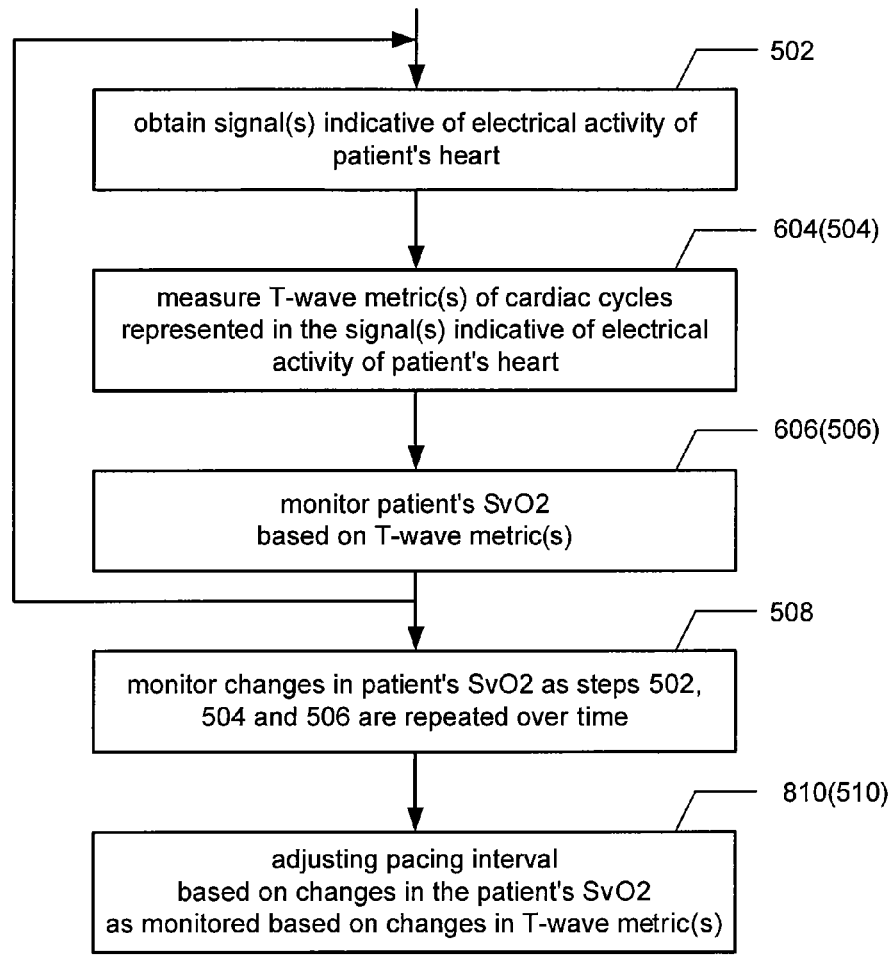
FIG. 8 is a high level flow diagram that is used to summarize how pacing intervals can be adjusted in accordance with embodiments of the present invention.

Referring now to FIG. 8, at step 810, which is a specific embodiment of step 810, one or more pacing interval is adjusted based on changes in SvO2, as monitored based on changes in measured T-wave metric(s). Exemplary pacing intervals include, but are not limited to, atrio-ventricular (RA-RV) delay, interventricular (RV-LV) delay, interatrial (RA-LA) delay and intraventricular ($RV_1$-$RV_2$ or $LV_1$-$LV_2$) delay. This can include adjusting the pacing interval(s) to attempt to maintain the patient's SvO2 at a specified level. As mentioned above with reference to step 710, the specified level can be an optimal level, e.g., as specified by a physician, or a maximum SvO2 level. In specific embodiments, step 810 includes increasing or decreasing specific pacing intervals, or combinations thereof, to attempt to increase the patient's SvO2.

More generally, the flow diagrams of FIGS. 7 and 8 show that SvO2, as measured based on T-wave metric(s), can be used as a measure of hemodynamic response when performing pacing optimization, including pacing rate and pacing delay optimization.

Figure 9:
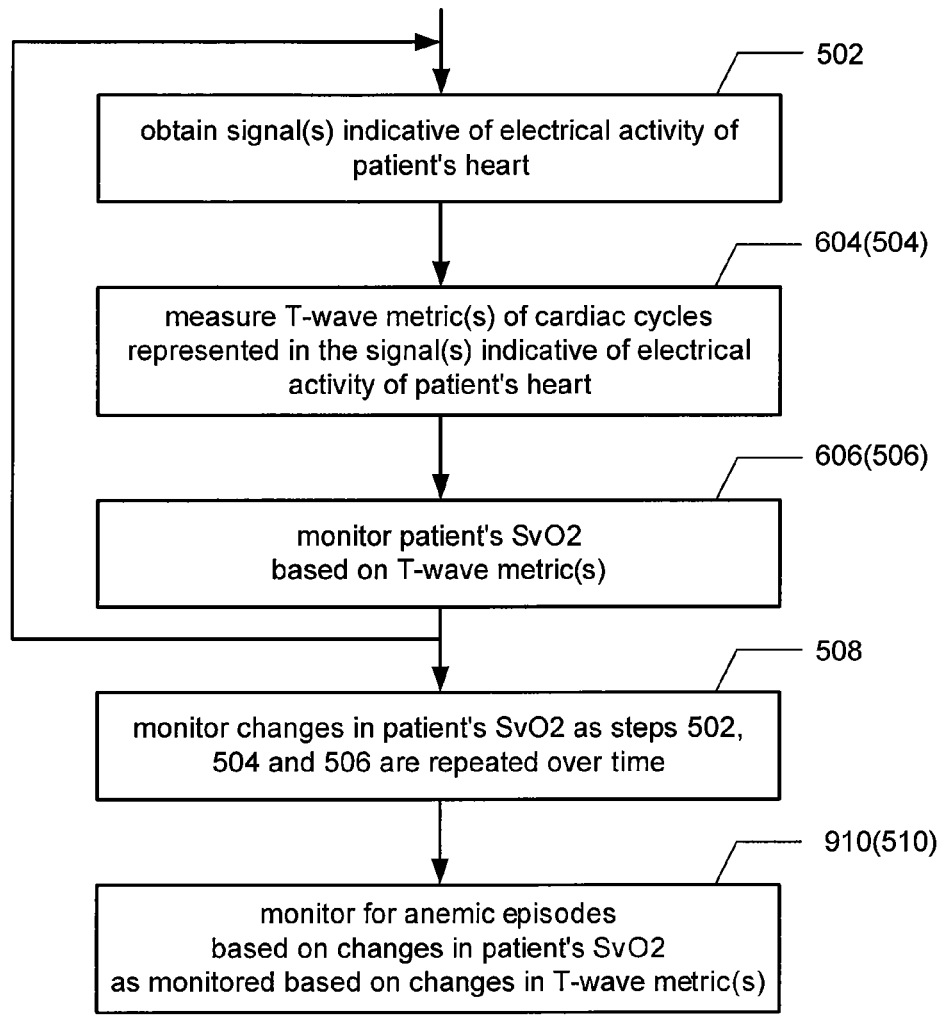
FIG. 9 is a high level flow diagram that is used to summarize how anemic episodes can detected in accordance with embodiments of the present invention.

Anemia is a deficiency of red blood cells (RBCs) and/or hemoglobin, which results in a reduced ability of blood to transfer oxygen to the tissues, causing tissue hypoxia. Referring now to FIG. 9, at step 910, anemic episodes are monitored for based on changes in the patient's SvO2 as monitored based on changes in T-wave metric(s). This can include interpreting transient decreases in the patient's SvO2 as being indicative of anemic episodes. To increase the specificity of detecting episodes of anemia, it may be prudent to use this monitoring technique in patient's known to have anemia and/or to use this monitoring technique together with another known technique for detecting anemic episodes, such as use of an infrared hemoglobin sensor. Assuming the device that monitors for anemic episodes is chronically implanted, the device can trigger an implanted patient alarm when anemic episodes are believed to be detected, and/or the device can transmit an alert (e.g., via telemetry) to an external monitor, which in turn can alert the patient and/or a caregiver. The device can also store data indicative of when the anemic episodes took place.

Figure 10:
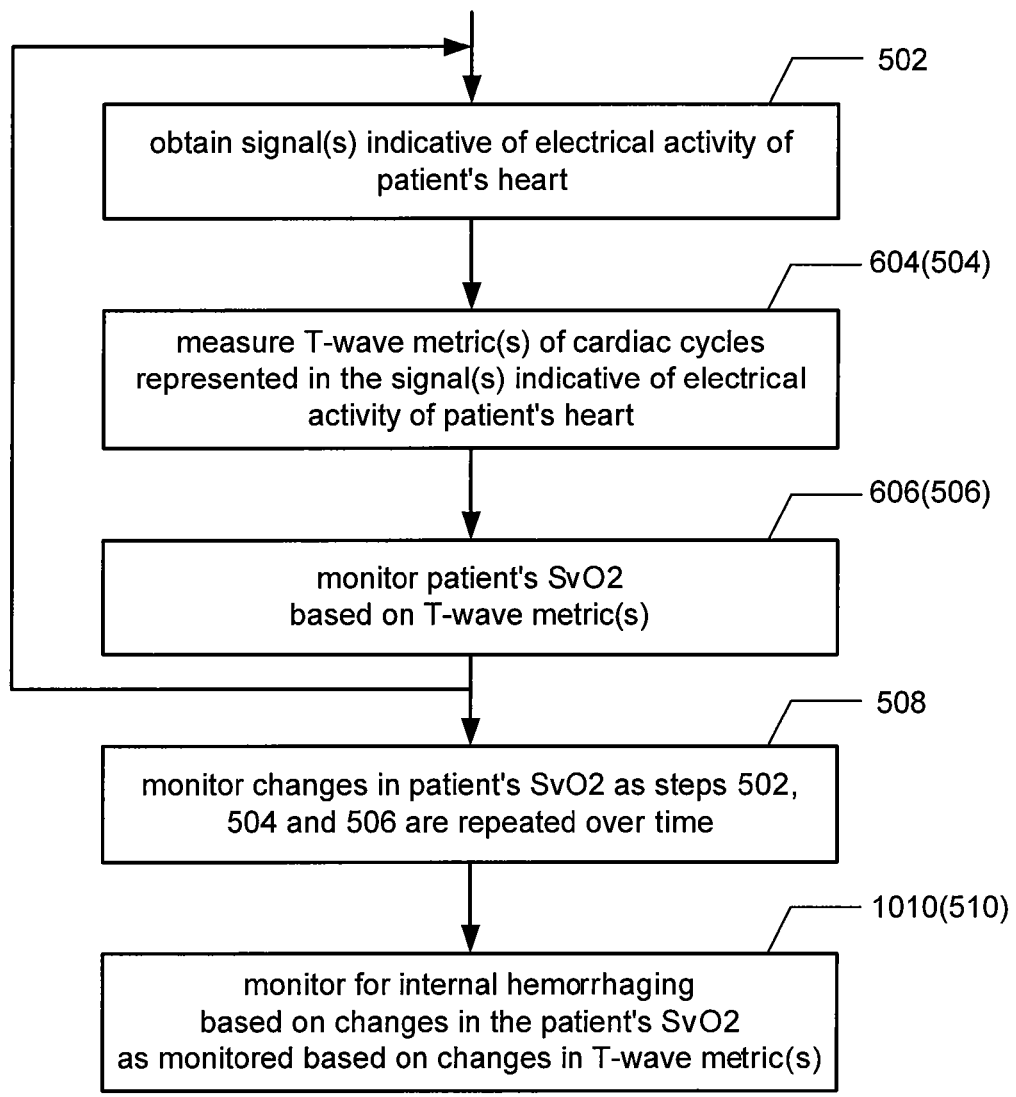
FIG. 10 is a high level flow diagram that is used to summarize how internal hemorrhaging can be detected in accordance with embodiments of the present invention.

Referring now to FIG. 10, at step 1010, internal hemorrhaging is monitored for based on changes in the patient's SvO2 as monitored based on changes in the at least one T-wave metric. This can include interpreting transient decreases in the patient's SvO2 as being indicative of internal hemorrhaging. To increase the specificity of detecting internal hemorrhaging, it may be prudent to use this monitoring technique in patient's known to have susceptibility to internal hemorrhaging and/or to use this monitoring technique together with another known technique for detecting internal hemorrhaging, such as by monitoring hematocrit (e.g., using an optical hematocrit sensor), where decreases of hematocrit are interpreted as being indicative of internal hemorrhaging. Assuming the device that monitors for internal hemorrhaging is chronically implanted, the device can trigger an implanted patient alarm when internal hemorrhaging is believed to be detected, and/or the device can transmit an alert (e.g., via telemetry) to an external monitor, which in turn can alert the patient and/or a caregiver. The device can also store data indicative of when the internal hemorrhaging took place.

Figure 11:
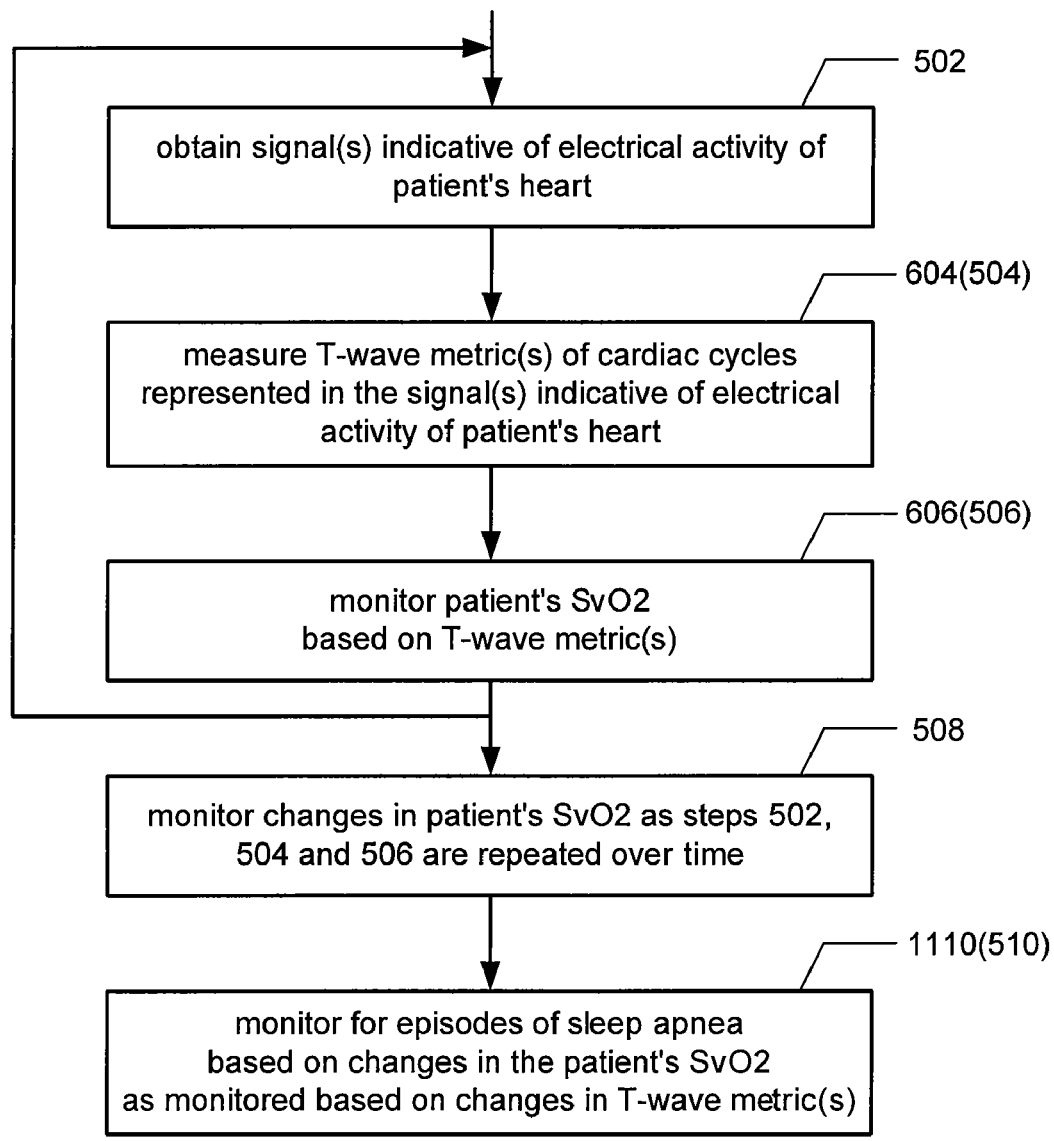
FIG. 11 is a high level flow diagram that is used to summarize how episodes of sleep apnea can be detected in accordance with embodiments of the present invention.

Sleep apnea is a disease in which breathing ceases during sleep. Referring now to FIG. 11, at step 1110, episodes of sleep apnea are monitored for based on changes in the patient's SvO2 as monitored based on changes in the at least one T-wave metric. This can include interpreting transient decreases in the patient's SvO2, while the patient is likely sleeping, as being indicative of episodes of sleep apnea. Information regarding whether it is likely that a patient is sleeping can be obtained, e.g., using sensor 215 in FIG. 2. It is noted that the term apnea as used herein is also meant to include hypopnea, which is generally defined as a decrease in airflow by at least 50% for ten seconds or more (as opposed to a substantially complete cessation of airflow).

In accordance with embodiments of the present invention, a patient can be stimulated in response to an episode of sleep apnea being detected. Such a stimulation can be, e.g., an electrical stimulation, an audible stimulation or a vibrating stimulation. The purpose of the stimulation would be to arouse the patient enough such that they begin a normal breathing pattern (e.g., by bringing them to a lighter state of sleep), preferably without completely waking the patient. If the device that is monitoring SvO2 is implanted, then the stimulation can be produced from within the patient by the implanted device housing the SvO2 monitor. Alternatively, an implanted device can trigger an non-implanted device (e.g., using telemetry) to provide the stimulation. The device can also store data indicative of when the episodes of sleep apnea took place, including the lengths of each episode.

The flow diagram of FIG. 12 is provided to summarize how PR intervals, measured in the signal obtained at step 502, can be the (or one of the) metric(s) that are measured to monitor SvO2, and changes therein. As was already discussed above with reference to FIGS. 5 and 4, it is believed that increases in PR intervals can be indicative of (and thus interpreted as) increases in SvO2, and vice versa. As was explained above when discussing QT intervals, PR intervals can also be normalized for heart rate, because PR intervals will decrease with increases in heart rate, and increase with decreases in heart rate, even when SvO2 remains the same.

In a similar manner as was discussed above with reference to FIG. 6, changes in the patient's HF condition can be monitored based on changes in the patient's SvO2 as monitored based on changes in PR intervals. Decreases in the patient's SvO2 over time can be interpreted as being indicative of worsening of the patient's heart failure, and increases in the patient's SvO2 over time can be interpreted as being indicative of improvement of the patient's heart failure.

In a similar manner as was discussed above with reference to FIGS. 6 and 7, pacing rate and pacing intervals can be adjusted based on changes in the patient's SvO2 as monitored based on changes in PR intervals, wherein the pacing rate and/or pacing interval(s) can be adjusted to attempt to maintain the patient's SvO2 at a specified level or optimum level.

In a similar manner as was discussed above with reference to FIG. 9, anemic episodes can be monitored for based on changes in the patient's SvO2 as monitored based on changes PR intervals. This can include interpreting transient decreases in a patient's SvO2 as being indicative of anemic episodes.

In a similar manner as was discussed above with reference to FIG. 10, internal hemorrhaging can be monitored for based on changes in the patient's SvO2 as monitored based on changes in PR intervals. This can include interpreting decreases in the patient's SvO2 as being indicative of internal hemorrhaging.

In a similar manner as was discussed above with reference to FIG. 11, episodes of sleep apnea can be monitored for based on changes in the patient's SvO2 as monitored based on changes in PR intervals. This can include interpreting transient decreases in the patient's SvO2, while the patient is likely sleeping, as being indicative of episodes of sleep apnea.

In many of the embodiments, pacing parameters are adjusted and episodes of a condition are detected based on changes in SVO2 as monitored based on changes in metric(s)

of an IEGM and/or ECG. It is noted that the term "based on", as used herein, means based at least in part on, unless stated otherwise. For example, in steps 710 and 810 where pacing adjustment/optimization is based on changes in the patient's SvO2, its possible that the measures of SvO2 are just one of many measures of hemodynamic response that are used in a pacing adjustment/optimization algorithm. For example, measures of SvO2 can be used, along with a weighting factor, in an algorithm that also takes into account mean arterial blood pressure, etc. For another example, in step 1110, other factors can be measured and taken into account, besides SvO2, when monitoring for episodes of sleep apnea.

The present invention has been described above with the aid of functional building blocks illustrating the performance of specified functions and relationships thereof. The boundaries of these functional building blocks have often been arbitrarily defined herein for the convenience of the description. Alternate boundaries can be defined so long as the specified functions and relationships thereof are appropriately performed. Any such alternate boundaries are thus within the scope and spirit of the claimed invention. For example, it would be possible to combine or separate some of the steps shown in FIGS. 4-12. Further, it is possible to change the order of some of the steps shown in FIGS. 4-12, without substantially changing the overall events and results.

The previous description of the preferred embodiments is provided to enable any person skilled in the art to make or use the embodiments of the present invention. While the invention has been particularly shown and described with reference to preferred embodiments thereof, it will be understood by those skilled in the art that various changes in form and details may be made therein without departing from the spirit and scope of the invention.

What is claimed is:

1. A method for monitoring a patient's venous blood oxygen saturation (SvO2), comprising:
   (a) obtaining at least one signal indicative of electrical activity of a patient's heart;
   (b) measuring at least one metric of cardiac cycles represented in the at least one signal indicative of electrical activity of the patient's heart, wherein the at least one metric changes with changes in SvO2; and
   (c) monitoring the patient's SvO2 based on the at least one metric.

2. The method of claim 1, wherein step (c) includes normalizing the at least metric before the patient's SvO2 is monitored based on the at least one metric.

3. The method of claim 1, wherein step (a) includes obtaining at least one intracardiac electrogram (IEGM) and/or at least one electrocardiogram (ECG).

4. The method of claim 1, further comprising:
   (d) monitoring changes in the patient's SvO2 as steps (a), (b) and (c) are repeated over time.

5. The method of claim 1, wherein:
   step (b) comprises measuring at least one T-wave metric of cardiac cycles represented in the at least one signal indicative of electrical activity of the patient's heart; and
   step (c) comprises monitoring the patient's SvO2 based on the at least one T-wave metric.

6. The method of claim 5, wherein step (b) includes measuring at least one of the following T-wave metrics of cardiac cycles:
   T-wave amplitude maximum;
   T-wave amplitude minimum;
   T-wave amplitude peak-to-peak;
   T-wave amplitude dispersion;
   T-wave centroid;
   QT interval;
   T-wave area;
   T-wave frequency content; and
   T-wave frequency spread.

7. The method of claim 5, further comprising:
   (d) monitoring changes in the patient's SvO2 as steps (a), (b) and (c) are repeated over time;
   wherein increases in the at least one T-wave metric are interpreted as increases in the patient's SvO2; and
   wherein decreases in the at least one T-wave metric are interpreted as decreases in the patient's SvO2.

8. The method of claim 7, further comprising:
   (e) monitoring changes in the patient's heart failure condition based on changes in the patient's SvO2 as monitored based on changes in the at least one T-wave metric;
   wherein decreases in the patient's SvO2 over time are interpreted as being indicative of worsening of the patient's heart failure; and
   wherein increases in the patient's SvO2 over time are interpreted as being indicative of improvement of the patient's heart failure.

9. The method of claim 7, further comprising:
   (e) adjusting a pacing rate based on changes in the patient's SvO2 as monitored based on changes in the at least one T-wave metric.

10. The method of claim 7, further comprising:
    (e) adjusting at least one pacing interval based on changes in the patient's SvO2 as monitored based on changes in the at least one T-wave metric.

11. The method of claim 7, further comprising:
    (e) monitoring for anemic episodes based on changes in the patient's SvO2 as monitored based on changes in the at least one T-wave metric;
    wherein transient decreases in the patient's SvO2 are interpreted as being indicative of anemic episodes.

12. The method of claim 7, further comprising:
    (e) monitoring for internal hemorrhaging based on changes in the patient's SvO2 as monitored based on changes in the at least one T-wave metric;
    wherein transient decreases in the patient's SvO2 are interpreted as being indicative of internal hemorrhaging.

13. The method of claim 7, further comprising:
    (e) monitoring for episodes of sleep apnea based on changes in the patient's SvO2 as monitored based on changes in the at least one T-wave metric;
    wherein transient decreases in the patient's SvO2, while the patient is likely sleeping, are interpreted as being indicative of episodes of sleep apnea.

14. The method of claim 1, wherein:
    step (b) comprises measuring PR intervals of cardiac cycles represented in the at least one signal indicative of electrical activity of the patient's heart; and
    step (c) comprises monitoring the patient's SvO2 based on the PR intervals.

15. The method of claim 14, further comprising:
    (d) monitoring changes in the patient's SvO2 as steps (a), (b) and (c) are repeated over time;
    wherein increases in the PR intervals are interpreted as increases in the patient's SvO2; and
    wherein decreases in the PR intervals are interpreted as decreases in the patient's SvO2.

16. The method of claim 15, further comprising performing at least one of the following based on changes in the patient's SvO2 as monitored based on changes in PR intervals:

(e.1) monitoring changes in the patient's heart failure condition based on changes in the patient's SvO2 as monitored based on changes in PR intervals, wherein decreases in the patient's SvO2 over time are interpreted as being indicative of worsening of the patient's heart failure, and increases in the patient's SvO2 over time are interpreted as being indicative of improvement of the patient's heart failure;

(e.2) adjusting a pacing rate based on changes in the patient's SvO2 as monitored based on changes in PR intervals;

(e.3) adjusting at least one pacing interval based on changes in the patient's SvO2 as monitored based on changes in PR intervals;

(e.4) monitoring for anemic episodes based on changes in the patient's SvO2 as monitored based on changes PR intervals, wherein transient decreases in the patient's SvO2 are interpreted as being indicative of anemic episodes;

(e.5) monitoring for internal hemorrhaging based on changes in the patient's SvO2 as monitored based on changes in PR intervals, wherein transient decreases in the patient's SvO2 are interpreted as being indicative of internal hemorrhaging; and (e.5) monitoring for episodes of sleep apnea based on changes in the patient's SvO2 as monitored based on changes in PR intervals, wherein transient decreases in the patient's SvO2, while the patient is likely sleeping, are interpreted as being indicative of episodes of sleep apnea.

17. A method for monitoring for changes in a patient's venous blood oxygen saturation (SvO2), comprising:
   (a) obtaining at least one signal indicative of electrical activity of a patient's heart;
   (b) measuring at least one metric of cardiac cycles represented in the at least one signal indicative of electrical activity of the patient's heart, wherein the at least one metric changes with changes in SvO2;
   (c) repeating steps (a) and (b) over time to thereby monitor changes over time in the at least one metric; and
   (d) monitoring changes in the patient's SvO2 based on the changes in the at least one metric.

18. The method of claim 17, wherein step (c) includes normalizing the at least one metric before changes in the at least one metric are monitored.

19. A system for monitoring a patient's venous blood oxygen saturation (SvO2), comprising:
   a sensing circuit to obtain at least one signal indicative of electrical activity of a patient's heart;
   a measure component to measure at least one metric of cardiac cycles represented in the at least one signal indicative of electrical activity of the patient's heart, wherein the at least one metric changes with changes in SvO2; and
   a monitor to monitor the patient's SvO2 based on the at least one metric.

20. The system of claim 19, wherein the system comprises an implantable system.

21. The system of claim 19, wherein the monitor monitors changes in the patient's SvO2 based on the changes in the at least one metric.

22. The system of claim 19, wherein the at least one metric comprises at least one of a T-wave metric and a PR interval.

23. The system of claim 19, wherein the measure component and the monitor are implemented by a microcontroller of an implantable device.

24. The system of claim 19, wherein the monitor normalizes that at least one metric before the monitor monitors the patient's SvO2 based on the at least one metric.

* * * * *